United States Patent [19]

Wagner et al.

[11] Patent Number: 4,680,275

[45] Date of Patent: Jul. 14, 1987

[54] HOMOGENEOUS FLUORESCENCE IMMUNOASSAY USING A LIGHT ABSORBING MATERIAL

[75] Inventors: Daniel B. Wagner; Robert A. Baffi, both of Raleigh, N.C.

[73] Assignee: Becton, Dickinson and Company, Franklin Lakes, N.J.

[21] Appl. No.: 700,578

[22] Filed: Feb. 11, 1985

[51] Int. Cl.$^4$ ............................................ G01N 33/543
[52] U.S. Cl. .................................... 436/518; 436/531; 436/537; 436/547; 436/800; 436/805; 436/808; 436/546; 436/524; 436/527; 436/532
[58] Field of Search ............... 436/537, 546, 547, 800, 436/805, 808, 518, 524, 527, 531, 532

[56] References Cited

U.S. PATENT DOCUMENTS

| | | | |
|---|---|---|---|
| 4,259,313 | 3/1981 | Frank | 436/800 |
| 4,318,707 | 3/1982 | Litman | 435/8 |
| 4,582,809 | 4/1986 | Block | 436/527 |

FOREIGN PATENT DOCUMENTS

0157197  10/1985  European Pat. Off. ............ 436/800

*Primary Examiner*—Sam Rosen
*Assistant Examiner*—Robert Benson
*Attorney, Agent, or Firm*—Richard E. Brown

[57] ABSTRACT

A method for separation-free solid phase immunoassay of an analyte includes contacting an anti-analyte attached to the surface of a solid support with the analyte, a light absorbing material and a fluorescent tracer for the analyte. The resulting mixture is incubated. The method includes applying excitation light to the mixture and time resolved measurement of fluorescence emission from the tracer. All excitation light and fluorescence emission are absorbed by the light absorbing material except that absorbed and emitted by the tracer bound to the anti-analyte whereby the only fluorescence emission detected is from the bound tracer. Since free tracer in the fluid phase of the assay medium does not emit fluorescence, separation of the bound and free fractions is unnecessary. The invention includes a kit of materials useful in performing an immunoassay in accordance with the method of the invention.

28 Claims, 3 Drawing Figures

HOMOGENEOUS FLUORESCENCE IMMUNOASSAY USING A LIGHT ABSORBING MATERIAL

BACKGROUND OF THE INVENTION

1. Field of the Invention

This invention relates to an immunoassay of an analyte and materials used therein, and more particularly relates to a method and materials for immunoassay which does not require separation of bound and free fractions.

2. Description of the Prior Art

A variety of assay systems which are both rapid and sensitive has been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer. Immunoassay procedures may be carried out in solution or on a solid support and may be either heterogeneous or homogeneous. Heterogeneous assays require a separation of bound tracer from free (unbound) tracer. Homogeneous assays do not require a separation step and thereby provide significant advantage in speed, convenience and ease of automation over heterogeneous assays.

Radioimmunoassay (RIA) procedures use radioisotopes as labels, provide high levels of sensitivity and reproducibility, and are amenable to automation for rapid processing of large numbers of samples. However, all RIA procedures require a separation step, since the parameter measured (nuclear decay) cannot be controlled by changing assay conditions or components. In addition, isotopes are costly, have relatively short shelf lives, require expensive and complex equipment, and extensive safety measures for their handling and disposal must be followed.

Enzymes have also been used as labels in immunoassay. Enzymeimmunoassay (EIA) may be homogeneous and does not require precautions against radioactivity. Conjugation of an enzyme with a protein is usually straightforward, and the resulting proteinenzyme conjugate is generally stable. However, EIA depends on the reaction of the enzyme conjugate with a substrate to produce a color which is measured, and thus requires the additional step of providing an enzyme substrate. In addition, sufficient time must be allowed for color development and an expensive spectrophotometer for measuring color change must be provided.

Some of the above disadvantages associated with RIA or EIA have been overcome by use of fluorochromes as labels in immunoassay. Fluoroimmunoassay (FIA) provides direct detection of the label and is readily adaptable to homogeneous assay procedures. However, known homogeneous FIA methods using organic fluorochromes, such as fluorescein or rhodamine derivatives, have not achieved the high sensitivity of RIA or EIA, largely because of light scattering by impurities suspended in the assay medium and by background fluorescence emission from other fluorescent materials present in the assay medium. Scattering is particularly troublesome with fluorochromes having a short (50 nm or less) Stoke's shift (the difference between the wavelength of the absorption and emmission). For example, the Stoke's shift of fluorescein isothiocyanate in only 20–30 nm. Background fluorescence is particularly troublesome when the assay medium is serum. The sensitivity of an assay in serum may be reduced up to one hundred fold compared to an identical assay in buffer.

The development of time-resolved fluoroimmunoassay (TR-FIA) has contributed to overcoming these problems. In this procedure, a fluorochrome label with a relatively long fluorescence emission decay time is excited with a pulse of light, and fluorescence emission from the label is measured after a preselected delay. Background emission of short decay time (generally less than 10 ns) essentially ceases during the delay and thereby does not interfere with measurement of the specific emission from the label. TR-FIA is most effective when the fluorescent label has a decay time of 100–1000 ns and a long Stoke's shift (100 nm or greater).

A class of labels meeting the requirements of TR-FIA is the lanthanide chelates. Lanthanide ions, in particular ions of europium and terbium form highly fluorescent chelates of long Stoke's shift (up to 250 nm) with organic ligands, in particular with $\beta$-diketones. The ligand portion of the chelate absorbs excitation light and transfers the absorbed energy to the chelated metal ion. The metal ion emits the energy as fluorescence of exceptionally long decay time (1 ms). A discussion of the use of lanthanide chelates in TR-FIA is given in Analytical Biochemistry, 137 335 (1984).

U.S. Pat. No. 4,058,732 to Wieder discloses a method and apparatus for use of lanthanide chelates and time resolution in analytical fluorescent spectroscopy.

U.S. Pat. No. 4,283,382 to Frank et al. discloses an improvement in TR-FIA in which a lanthanide chelate label is incorporated into a polymeric bead lattice to eliminate water-induced quenching of the fluorescence emission of the label.

U.S. Pat. No. 4,374,120 to Soini et al. discloses increased stability of lanthanide chelates achieved by a 1:1:1 chelate of lanthanide, $\beta$-diketone, and an aminopolycarboxylic acid analogue having a functional group useful for binding the chelate to a protein.

European patent application EP 0,064,484-A2 discloses a TR-FIA procedure in which the substance to be determined is coupled to an lanthanide by an aminocarboxylic acid analogue, and, after incubation, the lanthanide is split from the substance to be determined and chelated to a $\beta$-diketone before detection.

Although the above methods have improved FIA, there is still a need for a FIA of high sensitivity which can be carried out rapidly without requiring a separation of bound and free fractions.

SUMMARY OF THE INVENTION

One aspect of the present invention comprises a method for solid phase immunoassay of an analyte without separation of bound and free fractions. An antianalyte attached to the surface of a solid support is contacted with a fluid containing the analyte, a light absorbing material and a tracer for the analyte having an attached label which absorbs and emits light. After incubation of the assay mixture, excitation light is applied and light emission is measured by time resolution. The magnitude of light emission is compared with the magnitude of light emission measured when one or more known quantities of analyte is assayed under essentially identical conditions.

In a preferred embodiment of the method of the invention, the label is a fluorescent dye of relatively long decay time and the light absorbing material is a UV absorbing compound having an absorption band which overlaps the absorption band of the tracer.

In a particularly preferred embodiment of the method of the invention, the analyte is in a serum sample, the light-absorbing material is an arylaminonaphthalene sulfonic acid, the tracer is a lanthanide chelate incorporated into a polymeric particle attached to the analyte, and the tracer and the analyte compete for an insufficient number of anti-analyte binding sites.

In another embodiment of the method of the invention, substantially all of the analyte binds to both the anti-analyte and the tracer in a sandwich assay.

Another aspect of the invention includes a kit of materials for performing the method of the invention.

In accordance with the method of the invention, a solid phase TR-FIA is carried out which does not require a separation of bound and unbound fractions whereby operational simplicity, speed and convenience of homogeneous assays is achieved. The label is detected directly without an additional substrate or incubation period to generate a detectable material. The method of the invention provides a highly sensitive homogeneous assay essentially free of interfering emission from other fluorescent materials whereby an analyte present in very low concentration can be accurately determined. Because the procedure is exceptionally facile to carry out, it is readily adaptable to automation.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

In accordance with the method of the invention, the concentration of a substance present in a fluid may be determined by means of an immunological reaction. The substance, hereinafter referred to as the analyte, may be an antigen, a hapten, or an antibody, and may be present in any suitable fluid. For example, the fluid may be a buffer, saline, or a body fluid such as serum or urine. In some cases, the analyte may be isolated from a body fluid and subsequently be introduced into a different fluid, such as buffer, for determination.

By the term "immunological reaction," as used herein, is meant a specific binding reaction of an antigen and an antibody, a hapten and an antibody, or any appropriate analogue of an antigen, an antibody, or a hapten which also binds specifically.

The immunological reaction of the method of the invention is carried out on the surface of a solid support. As known in the art, the solid support may be any support which does not interfere with the assay. Exemplary of solid supports which may be used are glass and polymeric materials, such as polyethylene, polystyrene and the like. Such supports may be fabricated into any suitable shape, such as sheets, plates, wells, or, preferably, tubes. In the most preferred embodiment of the invention, the immunological reaction is carried out on the inside walls and bottom of a tube, preferably a plastic tube with one closed end.

An anti-analyte is attached to the surface of the solid support. The anti-analyte may be an antigen or an antibody which reacts specifically with the analyte, or it may be any appropriate analogue thereof which reacts specifically with the analyte. Attachment of the anti-analyte to the solid support may be carried out by any conventional procedure, such as, for example, absorption or covalent bonding. These procedures are well known in the art, and no further details in these respects are deemed necessary for a complete understanding of the invention.

The quantity of anti-analyte to be attached to the solid support depends on the type of assay to be carried out. In a competitive immunoassay as will first be described herein, a limited amount of anti-analyte is attached, whereby insufficient binding sites are available and the analyte and a tracer for the analyte, described below, compete for the available sites. In a sandwich assay, as will subsequently be described, excess anti-analyte is attached whereby essentially all analyte is bound to the anti-analyte.

In a competitive assay in accordance with the method of the invention, the anti-analyte attached to the solid support is contacted with an unknown quantity of analyte in a fluid, and the assay medium is incubated as described below to induce an immunological reaction between the analyte and anti-analyte. A tracer for the analyte is then added, and a subsequent incubation is carried out so that the assay medium contains free analyte, free tracer, bound analyte and bound tracer. Alternatively and preferably, the analyte and tracer are added simultaneously and a single incubation is carried out. Analyte and tracer bound to the anti-analyte on the solid support are hereinafter referred to as the bound fraction, and analyte and tracer which do not bind to the anti-analyte are hereinafter referred to as the free fraction.

The tracer provides a means to follow the course of the immunological reaction, and, in a competitive assay, preferably consists of a known quantity of the analyte or appropriate analogue thereof coupled to a label. The label may be any substance which absorbs and emits light and which may be coupled to the analyte. The preferred label emits light of long decay time, most preferably long decay fluorescence emission, which allows detection of the bound tracer without any substantial interference from other light emitting materials in the assay system. The most preferred labels absorb excitation light of wavelength about 280 to 375 nm, emit fluorescence of wavelength about 580 to 630 nm, and have a Stoke's shift of from about 200 to 250 nm. The decay time of the fluorescence emission of the most preferred labels is from about 0.5 to 1.0 ms.

Long decay time fluorescent labels useful in accordance with the method of the invention are pyrene derivatives and, preferably, the lanthanide chelates. The latter class of labels consists of a lanthanide ion, such as an ion of europium or terbium chelated with an organic ligand, as, for example, a $\beta$-diketone. Exemplary of $\beta$-diketones which can be used are benzoylacetone, dibenzoylmethane, thenoyltrifluoroacetone, benzoyltrifluoroacetone, naphthoyltrifluoroacetone, acetylacetone, trifluoroacetylacetone, hexafluoroacetylacetone, and the like. Chelation of the $\beta$-diketone with the lanthanide ion is routinely carried out by incubating the reagents for an appropriate time. The quantity of lanthanide chelate to be used in preparation of the tracer depends on the type of assay to be carried out and the quantity of analyte in the fluid, and is well known to those of ordinary skill in the art.

The lanthanide chelate label may be coupled directly to the analyte by conventional means to produce the tracer. Alternatively and preferably, the label is incorporated into a particle, and the particle is attached to the analyte to give the tracer. The particle may be a polymeric particle, such as a bead. Any polymer may be used which is capable of incorporation of the label and attachment to the analyte. The preferred polymers are essentially transparent to both the excitation light and the fluorescence emission, and do not enter into any substantial number of non-specific surface reactions with proteins other than the analyte, as, for example, other proteins in serum. A particularly preferred polymer for incorporation of the label is a polyacrylate, as, for example, polymethylmethacrylate.

The label is incorporated into the particle by conventional methods. For example, a polymeric particle containing the label may be prepared by emulsion polymerization of a monomer in a solution containing the label. Likewise, the particle is attached to the analyte by conventional means, preferably by covalent coupling of appropriate functional groups on the analyte and on the surface of the particle. The conventional methods for incorporation of the label into the particle and attachment of the particle to the analyte are well known and are deemed to be within the purview of those skilled in the art, and no further details with regard to those elements are necessary for a complete understanding of the invention.

The assay medium containing the supported antianalyte, the fluid containing the analyte, and the tracer may be incubated at any temperature and for any length of time suitable to facilitate the immunological reaction and thereby provide the aforementioned bound and free fractions. The incubation may be carried out at a temperature from about 0° to 50° C., preferably from about 30° to 40° C., and may, but need not, result in equilibrium between these fractions.

A light absorbing material is added to the assay system either before or after the immunological reaction, and may be any material which has an absorption band which overlaps the absorption band of the tracer and which does not interfere with the immunological reaction. Suitable absorbing materials are exemplified by, but not limited to, stilbenes, benzoxazoles, naphthalenes and derivatives thereof. A preferred group is the arylaminonaphthalene sulfonic acids, as, for example, 2-(p-anisidinyl) naphthalene-6-sulfonic acid or 1-anilinononaphthalene-8-sulfonic acid (1,8-ANS). The concentration of absorbing material in the assay medium may be from about $10^{-2}$ to $10^{-6}$M, preferably from about $10^{-3}$ to $10^{-4}$M.

Bound tracer is detected by applying excitation light and measuring light emission from the label in the presence of the light absorbing material. The excitation light preferably has a wavelength within the absorption range of the label used. When the label is a lanthanide chelate, the excitation light preferably has a wavelength of from about 280 to 375 nm, most preferably about 343 nm and is discontinuous, i.e., pulses of light alternate with periods when the light source is off. The light pulses may be from about 0.1 to 10 $\mu$s, preferably about 3 $\mu$s in duration. The periods when the light source is off may be from about 0.1 to 2.0 ms, preferably about 0.9 ms.

Light emission is preferably measured by time-gating after a delay of about 0.1 to 0.5 ms, preferably about 0.5 ms from completion of a pulse. The wavelength of the light emission depends on the label used. When the label is a lanthanide chelate, the emission wavelength generally is from about 580 to 630 nm. Most preferably, emission is measured at a wavelength of about 614 nm.

Measurement of light emission by time-gating in accordance with the preferred method of the invention may be carried out in a conventional spectrophotometer, as, for example, a Spex L-111 fluorimeter (SPEX Industries, Inc., Edison, N.J.) equipped with a gated photon detector. Emission may be measured at any angle to the beam of excitation light. Preferably, emission is measured at an angle of about 2-20 degrees from the beam of excitation light.

The light absorbing material in the fluid phase of the assay system absorbs all excitation and/or emission light which passes through the fluid phase and thereby effectively prevents detection of emission from free tracer. On the other hand, bound tracer absorbs and subsequently emits detectable light which has not passed through the fluid phase.

Figure 1:
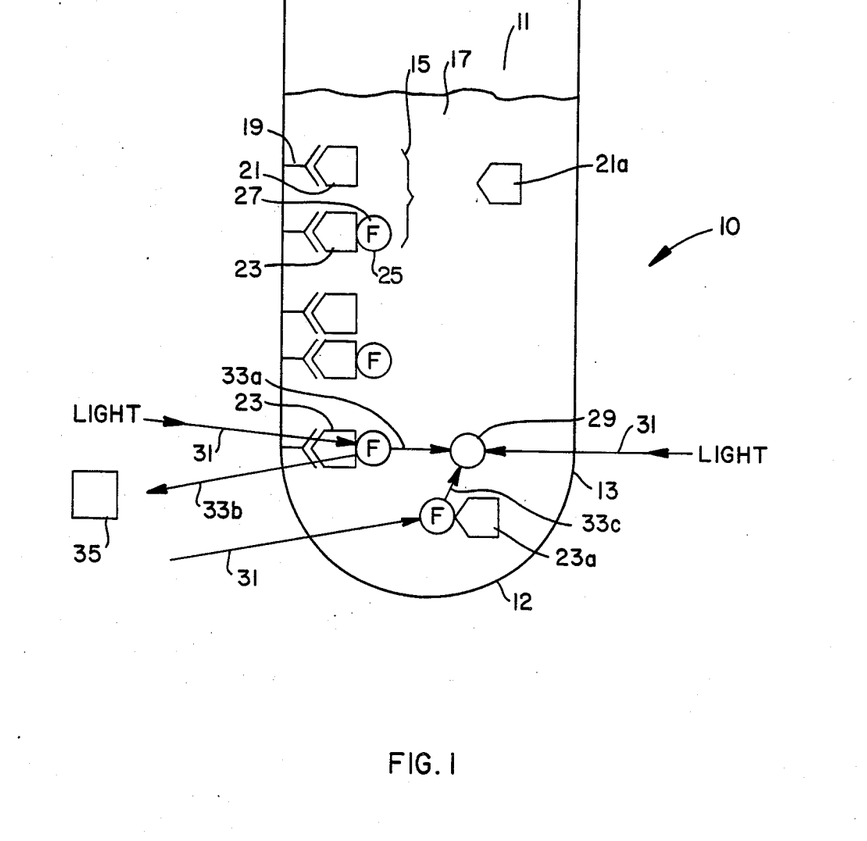
FIG. 1 shows a tube and other components of use in a competitive immunoassay in accordance with the method of the invention.

The method and components of the invention are depicted in FIG. 1 wherein assay system 10 includes a preferably polystyrene tube 13 having an open end 11 and a closed end 12. Tube 13 contains a bound fraction 15 and fluid phase 17. Bound fraction 15 includes antianalyte 19 attached to the inside walls of tube 13 and bound analyte 21 and bound tracer 23. Bound tracer 23 comprises bound analyte 21 having attached polymeric particle 25 with incorporated fluorescent dye label 27. Fluid phase 17 includes free analyte 21a, free tracer 23a and light absorbing material 29.

Excitation light, schematically illustrated by reference line 31, passes through tube 13 and is absorbed by material 29, or it may pass through tube 13 and be absorbed by bound tracer 23 or free tracer 23a. Fluorescence emission from bound tracer 23 includes emission 33a into fluid phase 17 where it is absorbed by material 29, and emission 33b outwardly through tube 13 without passing through fluid phase 17 where it is detected by fluorimeter 35. Emission 33c from free tracer 23a into fluid phase 17 is absorbed by material 29.

Excitation light reflected from the solid support does not interfere with measurement of emission from bound tracer because emission is measured when the light source is off. Short decay time background light emission associated with serum or other fluorescent materials in the assay medium, including that associated with the solid support itself, is essentially eliminated by time-resolved measurement of emission. Thus, in accordance with the method of the invention, the only light emission detected is from the tracer bound to the surface of the solid support.

In a competitive assay as hereinabove described, the magnitude of the light emission is directly proportional to the quantity of bound tracer and therefore is inversely proportional to the quantity of analyte present in the fluid. The concentration of the analyte in the fluid may be determined by comparing the magnitude of light emission measured upon assay of the analyte with the emission measured upon assay of a range of known quantities of the analyte assayed under essentially identical conditions.

The method of the invention may be adapted to a solid phase sandwich assay. This type of assay is particularly useful for assay of a macromolecular analyte, as, for example, a protein. Any modification of solid phase sandwich assay may be used. For example, the anti-analyte may be attached to the solid support in sufficient quantity to bind essentially all of the analyte through a first determinant on the analyte. The supported anti-analyte may be incubated with the analyte, the light absorbing material and a tracer wherein the tracer comprises a labeled ligand specific for a second determinant on the analyte. The ligand may be an antigen, an antibody or a bound antigen-antibody complex.

The preferred label and light absorbing material and the preferred method for excitation and detection of emission may be as described above for the competitive assay. However, in the sandwich assay of this embodiment of the invention, the concentration of the analyte present in the fluid is directly proportional to the magnitude of light emission.

In accordance with another aspect of the invention, there is provided a reagent kit or package of materials for accomplishing an assay for an analyte in accordance with the method of the invention. The kit may include a solid support having attached thereto an anti-analyte specific to the analyte, a light absorbing material, and a tracer for the analyte having attached thereto a label capable of absorbing excitation light and emitting detectable light. The kit may also include standards for the analyte, as, for example, one or more analyte samples of known concentration, or it may include other reagents, such as other labeled or unlabeled specific antigens, antibodies or complexes thereof useful in carrying out the assay. The components of the kit may be supplied in separate containers, as, for example, vials, or two or more of the components may be combined in a single container.

The following examples of a model system and an assay for digoxin are provided to further describe the invention, but are not intended in any way to be limitative of the invention.

EXAMPLE I

Polymethylmethacrylate beads of about 150 nm containing about 1% naphthoyltrifluoroacetone-europium chelate ($NTFA_3Eu$) were suspended in water and sprayed onto the surface of polystyrene cuvettes. The cuvettes were dried overnight at ambient temperature whereby the beads adhered to the surface and were not removed by washing with water. The cuvettes thus coated were used to represent the bound fraction of a TR-FIA, i.e., the solid support with attached anti-analyte and tracer.

An aqueous suspension of about $1 \times 10^4$ beads per ml was added to all cuvettes to represent the fluid phase of a TR-FIA containing free tracer.

Aqueous solutions of 1,8-ANS of the concentrations given in Table I were added to the cuvettes. One control cuvette received water only.

Using a Spex L-111 fluorimeter equipped with a gated photon detector, pulsed excitation light at 343 nm was applied at a right angle to the cuvettes. Fluorescence emission at 614 nm was measured, after a delay of 0.5 ms, at angles of 11° and 90° to the beam of excitation light. The results are given in Table I and show the effect of 1,8-ANS concentration on the fluorescence emission of the suspended beads.

TABLE I

| Concentration of 1,8-ANS | Number of Photons Detected | |
|---|---|---|
| (moles per liter) | 11° | 90° |
| 0 | 31,500 | 32,300 |
| $1 \times 10^{-2}$ | 1,300 | 45 |
| $1 \times 10^{-3}$ | 1,300 | 876 |
| $1 \times 10^{-4}$ | 27,200 | 31,400 |

It is seen that 1,8-ANS having a concentration of $1 \times 10^{-3}$ M eliminated all emission except that attributed to the bound beads.

EXAMPLE II

Two groups of three cuvettes each were coated, as described in Example I, with two different concentrations of beads. One cuvette in each group received water and represented the bound fraction of a TR-FIA. A second cuvette in each group received a suspension of the beads and represented the bound and free fractions of a TR-FIA. The third cuvette in each group received a suspension of the beads containing $5 \times 10^{-3}$ M 1,8-ANS.

Excitation and measurement of fluorescence emission at 11° were carried out as described in Example I. The results are given in Table II.

TABLE II

| | Number of Photons Detected | |
|---|---|---|
| | Cuvette 1 | Cuvette 2 |
| Coated Cuvette + Water (Bound Fraction) | 2,300 | 40,000 |
| Coated Cuvette + Suspended Beads (Bound and free fractions) | 32,400 | 71,000 |
| Coated Cuvette + Suspended Beads + $5 \times 10^{-3}$ M 1,8-ANS (Bound and free fractions and light absorbing material) | 2,700 | 38,000 |

It is seen that, in the presence of the absorbing material, the beads on the cuvette surface (bound fraction) were selectively excited and their fluorescence emission detected in the presence of a large excess of beads in suspension (free fraction).

EXAMPLE III

A. Preparation of the Fluorescent Polymer Particles

A polymer bead consisting of a 92:6:2 ratio of butyl methacrylate:glycidyl methacrylate:sulfoethyl methacrylate containing 1% $NTFA_3Eu$ was prepared in the following manner. Bis methylene acrylamide (0.05 g) and polyethylene oxide (0.1 g) were dissolved in deionized water (25 ml) and acetone (4 ml). A second solution was prepared which contained butyl methacrylate (0.78 ml), sulfoethyl methacrylate (0.2 g), glycidyl methacrylate (0.5 ml) and $NTFA_3Eu$ (25 mg). The two solutions were mixed together and the pH adjusted to 5.5 with 1N NaOH. After stirring well under $N_2$, the mixture was irradiated for 12 hr at 7.05 Mr/hr. The white emulsion was spun in a centrifuge at successively increased speeds. The pellet which was collected at 30,000 rpm was washed three times with 0.1% polyoxyethylenesorbitan monolaurate (Tween 20) in phosphate buffered saline (PBS-0.01M mixture of mono and di sodium phosphate in 0.15M NaCl). The pellet was ultimately suspended in a 10% solution of 1,3-diaminopropane in which the pH was adjusted to 10 with 1N HCl. The suspension was stirred overnight and then washed three times and suspended in 30 ml of PBS.

B. Preparation of the BSA-Digoxin Particle Conjugate

A sample (1.0 ml) of the particle suspension described in A was activated by the addition of glutaraldehyde at a final concentration of 1%. A 4 hr incubation was followed by three washings in PBS. To 1 ml of the activated beads was added 5 mg of a bovine serum albumin (BSA)-Digoxin conjugate. The mixture was stirred overnight at room temperature. The beads were washed three times, suspended in 25 ml of PBS, and stored at 4° C.

C. Coating of Polystyrene Cuvettes with Rabbit Anti-Digoxin Immunoglobulin

A two thousandfold dilution of rabbit anti-Digoxin Immunoglobulin was made into 0.1M carbonate buffer, pH 9.5. This solution was pipetted to the 3 ml level of the cuvettes. After incubation at room temperature for 4 hr, the cuvettes were aspirated and washed successively with a 2% BSA solution in PBS and finally in PBS. The cuvettes were dried and stored at 4° C.

D. Determination of a Standard Curve for Digoxin in Phosphate Buffer

Figure 2:
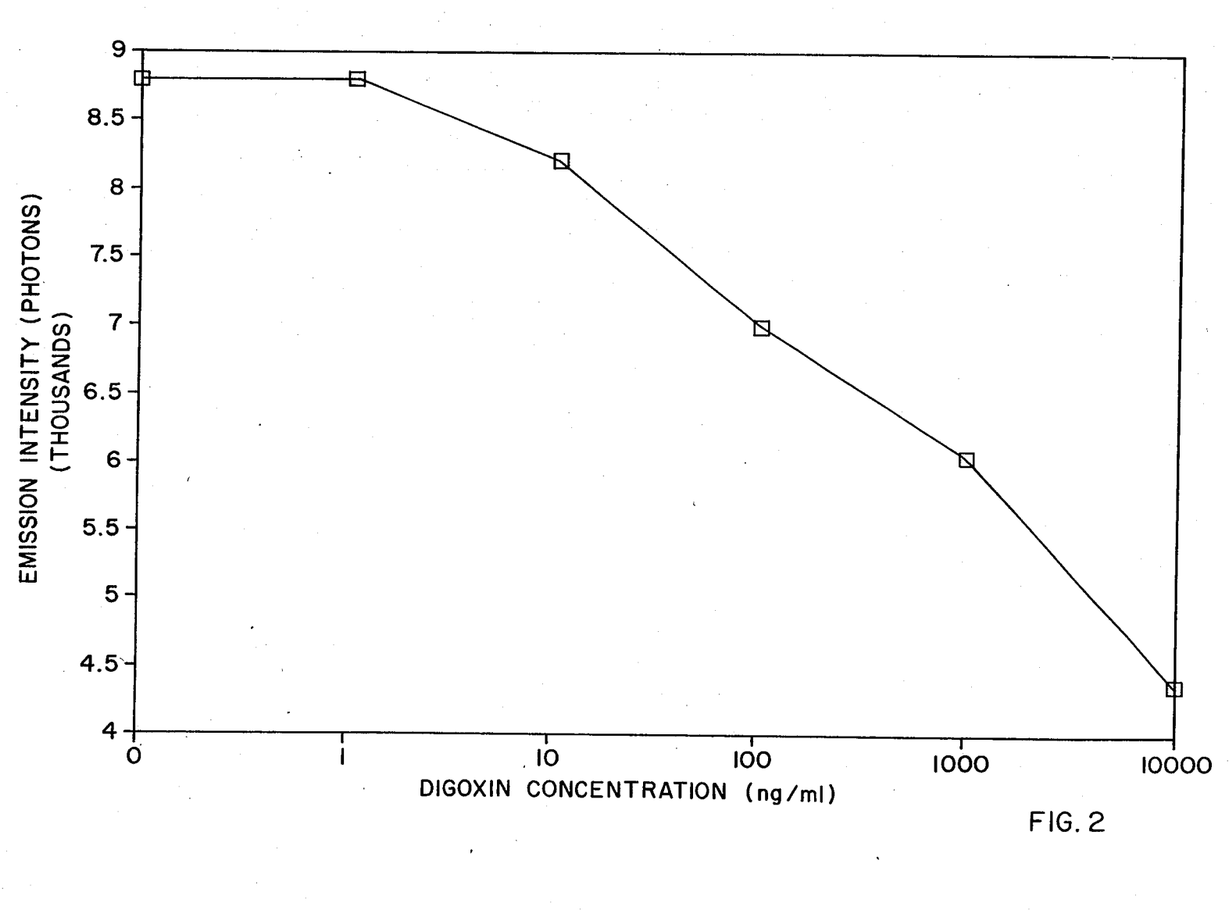
FIG. 2 is a standard curve of an assay for digoxin in accordance with the method of the invention.

Duplicate dilution series of Digoxin were made in PBS containing BSA (2%) and Tween 20 (0.5%) in the range of 1–10,000 ng/ml and then 3 ml each of these solutions and of blank PBS were pipetted into the cuvettes which had previously been coated as described in C. To each of these cuvettes was added 30 μl of the BSA-Digoxin particle conjugate prepared in section B. The cuvettes were incubated at 37° C. for 45 min. To each of the cuvettes was added 0.1M 1,8-ANS (30 μl) and fluorescence emission at 614 nm was measured after a delay of 0.5 ms at an angle of 11° to the beam of excitation light. The results are given in Table III and FIG. 2.

TABLE III

| Digoxin Concentration (ng/ml) | Intensity (photons) |
|---|---|
| 0 | 8700 |
| 1 | 8700 |
| 10 | 8200 |
| 100 | 7000 |
| 1000 | 6100 |
| 10000 | 4500 |

EXAMPLE IV

A. Preparation of Anti-HCG Immunoglobulin Particle Conjugate

A sample (1.0 ml) of the particle suspension described in Example IIIA was activated by the addition of glutaraldehyde at a final concentration of 1%. A 4 hr incubation was followed by three washings in PBS. To 1 ml of the activated beads were added 50 μl of a 1 mg/ml solution in PBS of a monoclonal antibody designated HCG-13 raised in the conventional way against HCG. The mixture was stirred overnight at room temperature. The beads were washed three times, suspended in 25 ml of PBS, and stored at 4° C.

B. Coating of Polystyrene Cuvettes with Monoclonal Anti-HCG-4 Immunoglobulin

A five thousandfold dilution of a second monoclonal antibody raised against HCG designated HCG-4, was made into 0.1M carbonate buffer, pH 9.5. This solution was pipetted to the 3 ml level of the cuvettes. After incubation at room temperature for 4 hr, the cuvettes were aspirated and washed successively with a 2% BSA solution in PBS and finally in PBS. The cuvettes were dried and stored at 4° C.

C. Determination of a Standard Curve for HCG in Phosphate Buffer

Figure 3:
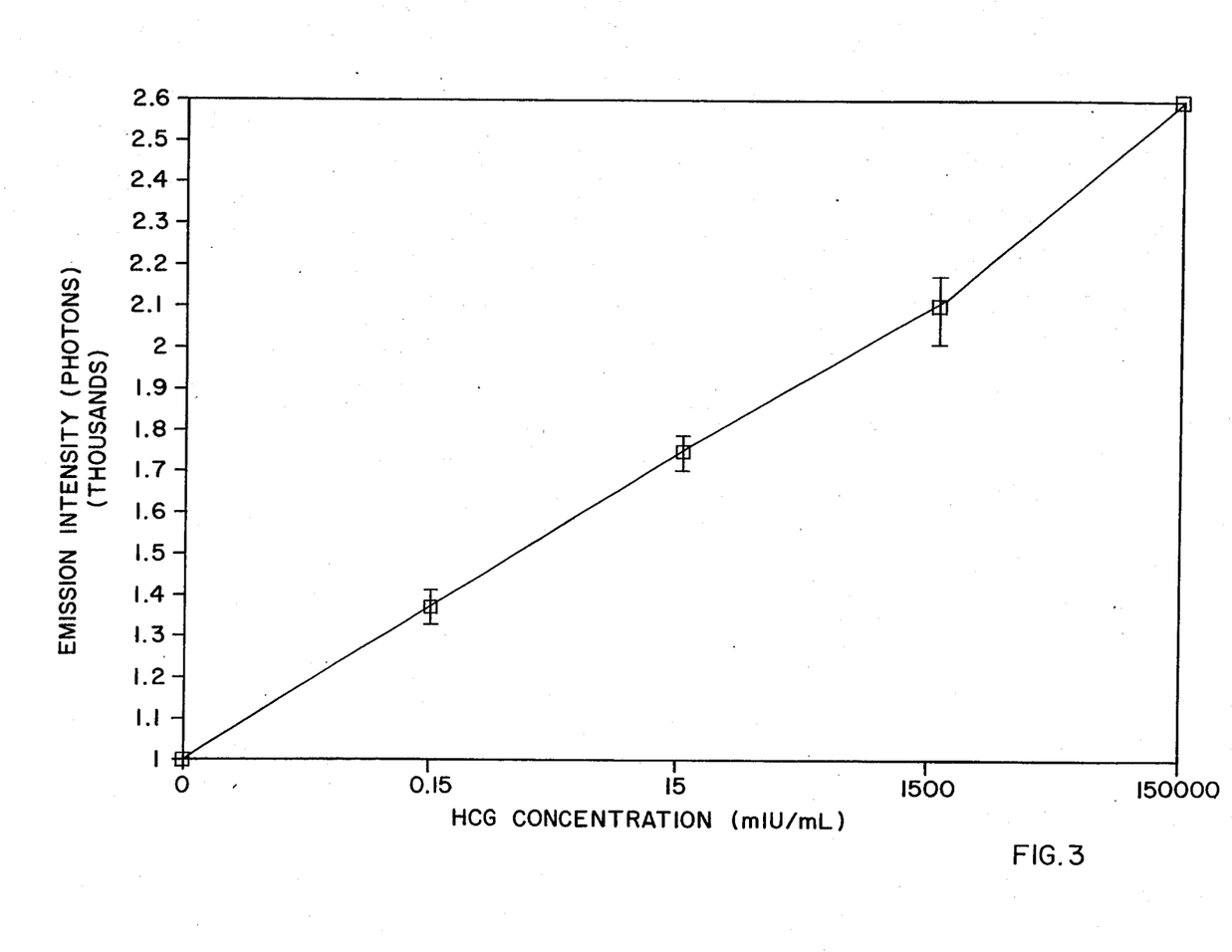
FIG. 3 is a standard curve of an assay for human chorionic ganadotropin (HCG) in accordance with the method of the invention.

Duplicate dilution series of HCG were made in PBS of 10 fold concentration in the range of $0.15-1.5 \times 10^5$ mIU/ml. These solutions and a blank PBS were pipetted into the cuvettes which had previously been coated as described in B. After a 1 hr incubation at 37° C., the microbeads (50 μl) described in A were added, and incubation was continued for another hr. To each of the cuvettes was added 0.1M 1,8-ANS (30 μl), and fluorescence emission at 614 nm was measured after a delay of 0.5 ms at an angle of 11° to the beam of excitation light. The results are given in Table IV and FIG. 3.

TABLE IV

| HCG Concentration (mIU/ml) | Intensity (photons) |
|---|---|
| 0 | 1,000 |
| 0.15 | 1,380 |
| 15 | 1,750 |
| 1,500 | 2,000 |
| 150,000 | 2,600 |

Thus, in accordance with the invention, a method for solid phase fluoroimmunoassay includes addition of a light absorbing material to the fluid phase of the assay system. The light absorbing material absorbs all excitation and/or emitted light except that absorbed by and emitted from bound tracer, whereby the emission from the bound tracer can be detected and measured in the presence of a large excess of free tracer. Separation of the bound and free fractions is thus avoided and the simplicity and convenience of a homogeneous assay is gained. By measuring light emission from the bound tracer using time resolution, interference from reflected excitation light and from light scattering and background emission can be minimized whereby higher assay sensitivity can be achieved. The method is easily adaptable to all modifications of solid phase competitive and sandwich type assay systems. The invention includes a kit of assay materials which can be used for either manual or automated assay.

What is claimed is:

1. A method for determining an unknown quantity of an analyte present in a fluid comprising:
    (a) preparing a mixture by contacting an anti-analyte attached to the surface of a light transmitting solid support with a fluid containing an unknown quantity of an analyte, a tracer consisting of a fluorescent dye conjugated to said analyte or to a ligand specific for said analyte, and a light absorbing material having an absorption band which overlaps the absorption band of said tracer;
    (b) incubating said mixture;

(c) applying to said mixture a pulse of excitation light through said solid support, the intensity and duration of said pulse being sufficient to cause the absorption of a portion of said excitation light by said tracer;

(d) detecting fluorescence emission from bound tracer, said emission being of sufficiently long decay time to be detected subsequent to completion of said light pulse and subsequent to the decay of substantially all light emission due to components of said mixture other than said bound tracer; and (e) determining the quantity of said analyte in said fluid by comparing the magnitude of said fluorescence emission with the magnitude of fluorescence emission established for a known quantity of the analyte.

2. The method in accordance with claim 1 wherein said analyte is selected from the group of analytes consisting of an antigen, a hapten and an antibody, and said anti-analyte is selected from the group of anti-analytes consisting of an antigen and an antibody.

3. The method in accordance with claim 1 wherein said tracer consists of said analyte having said fluorescent dye attached thereto, and wherein said tracer reacts specifically with said anti-analyte.

4. The method in accordance with claim 3 wherein a limited amount of said anti-analyte is attached to said support and said analyte and said tracer bind competitively to said anti-analyte.

5. The method in accordance with claim 1 wherein said tracer is selected from the group of tracers consistig of an antigen, an antibody and a bound antigen-antibody complex having said fluorescent dye attached thereto and wherein said tracer reacts specifically with said analyte.

6. The method in accordance with claim 5 wherein substantially all of said analyte binds to said anti-analyte and said tracer binds to said analyte.

7. The method in accordance with claim 1 wherein said fluorescent dye is a lanthanide chelate.

8. The method in accordance with claim 7 wherein said lanthanide chelate is incorporated into a polymeric particle.

9. The method in accordance with claim 1 wherein said fluid is serum.

10. The method in accordance with claim 1 wherein said light absorbing material is an arylaminonaphthalene sulfonic acid.

11. The method in accordance with claim 7 wherein the intensity of said pulse is from about $1 \times 10^{40}$ to $2 \times 10^{40}$ photons.

12. The method in accordance with claim 7 wherein the duration of said pulse is from about 1 to 10 μs.

13. The method in accordance with claim 7 wherein said pulse has a wavelength of from about 280 to 375 nm.

14. The method in accordance with claim 7 wherein said fluorescence emission has a wavelength of from about 580 to 630 nm.

15. The method in accordance with claim 7 wherein said fluorescence emission has a decay time of from about 0.5 to 1.0 ms.

16. The method in accordance with claim 1 wherein said fluorescence emission is measured between consecutive pulses.

17. The method in accordance with claim 1 wherein said fluorescence emission is measured between 0.5 and 0.75 ms after completion of a pulse.

18. The method in accordance with claim 1 wherein said fluorescence emission is measured at an angle of from 2 to 20 degrees from the direction of said pulse of excitation light.

19. A method for determining an unknown quantity of an analyte in a fluid comprising:
(a) preparing a mixture by contacting an anti-analyte attached to the surface of a light transmitting solid support with a fluid containing an unknown quantity of an analyte, a tracer consisting of a conjugate of a fluorescent dye with said analyte, and a light absorbing material having an absorption band which overlaps the absorption band of said tracer;
(b) allowing the elapse of a period of time sufficient to cause binding of said analyte and said tracer to said anti-analyte;
(c) applying excitation light to said mixture through said solid support;
(d) detecting time resolved light emission from bound tracer; and
(e) determining the quantity of said analyte in said fluid by comparing the magnitude of said detected light emission with the magnitude of light emission established for a known quantity of said analyte.

20. A method for determining an unknown quantity of analyte present in a serum sample comprising:
(a) preparing a mixture by contacting an anti-analyte attached to the surface of a light transmitting solid support wherein the quantity of anti-analyte binding sites available is insufficient to bind all of an analyte, with a serum sample containing an unknown quantity of said analyte, an arylaminonaphthalene sulfonic acid, and a tracer consisting of said analyte having attached thereto a particle having incorporated therein a lanthanide chelate label;
(b) incubating said mixture;
(c) applying to said mixture through said solid support a pulse of excitation light of wavelength about 280 to 375 nm, said pulse having an intensity of about $1 \times 10^{40}$ to $2 \times 10^{40}$ photons and a duration of about 1 to 10 μs;
(d) detecting fluorescence emission having a wavelength of about 580 to 630 nm and a decay time of about 0.5 to 1.0 ms from bound tracer, said emission being measured between consecutive excitation pulses at an angle of about 2 to 20 degrees from the direction of said pulse and about 0.50 to 0.75 ms after completion of a pulse; and
(e) determining the quantity of said analyte in said serum sample by comparing the magnitude of said fluorescence emission with the magnitude of fluorescence emission detected when a mixture containing a known quantity of said analyte is determined in accordance with steps (a) to (e).

21. The method in accordance with claim 20 wherein said particle is a polymeric particle.

22. The method in accordance with claim 20 wherein said lanthanide chelate is a europium or terbium ion chelated to a β-diketone.

23. A method for determining an unknown quantity of analyte present in a serum sample comprising:
(a) preparing a mixture by contacting an anti-analyte attached to the surface of a light transmitting solid support wherein the quantity of anti-analyte binding sites available is sufficient to bind essentially all of an analyte with a fluid containing an unknown quantity of said analyte, an arylaminonaphthalene sulfonic acid, and a tracer consisting of a ligand specific for said analyte, said ligand having attached thereto a particle having incorporated therein a lanthanide chelate label;

(b) incubating said mixture;

(c) applying to said mixture, through said solid support, a pulse of excitation light of wavelength about 280 to 375 nm, said pulse having an intensity of about $1 \times 10^{40}$ to $2 \times 10^{40}$ photons and a duration of about 1 to 10 $\mu s$;

(d) detecting fluorescence emission having a wavelength of about 580 to 630 nm and a decay time of about 0.5 to 1.0 ms, said emission being measured between consecutive excitation pulses at an angle of about 2 to 20 degrees from the direction of said pulse and about 0.5 to 0.75 ms after completion of a pulse; and (e) determining the quantity of said analyte in said serum sample by comparing the magnitude of said fluorescence emission with the magnitude of fluorescence emission when a mixture containing a known quantity of said analyte is determined in accordance with steps (a) to (e).

24. The method in accordance with claim 23 wherein said particle is a polymeric particle.

25. The method in accordance with claim 23 wherein said ligand is selected from the group of ligands consisting of an antigen, an antibody and a bound antigen-antibody complex.

26. The method in accordance with claim 23 wherein said lanthanide chelate is a europium or terbium ion chelated to a $\beta$-diketone.

27. A kit of materials for performing an assay for an unknown quantity of an analyte in a fluid comprising a light transmitting solid support having attached thereto an anti-analyte specific to an analyte, a tracer consisting of a fluorescent dye conjugated to said analyte or to a ligand specific for said analyte and a light absorbing material having an absorption band which overlaps the absorption band of said tracer.

28. The kit in accordance with claim 27 further comprising at least one analyte sample of known concentration.

* * * * *